US006797242B2

(12) United States Patent
Neumann et al.

(10) Patent No.: US 6,797,242 B2
(45) Date of Patent: Sep. 28, 2004

(54) SYSTEM FOR CHEMICAL AND BIOLOGICAL DECONTAMINATION

(75) Inventors: David K. Neumann, Colorado Springs, CO (US); Thomas L. Henshaw, Monument, CO (US); Jason K. Brasseur, Colorado Springs, CO (US)

(73) Assignee: Neumann Information Systems, Inc., Colorado Springs, CO (US)

( * ) Notice: Subject to any disclaimer, the term of this patent is extended or adjusted under 35 U.S.C. 154(b) by 306 days.

(21) Appl. No.: 10/099,049

(22) Filed: Mar. 15, 2002

(65) Prior Publication Data

US 2003/0175179 A1 Sep. 18, 2003

(51) Int. Cl.$^7$ .................................................. B01J 19/08
(52) U.S. Cl. ..................................... 422/186.3; 422/186
(58) Field of Search ............................... 422/186, 186.3

(56) References Cited

U.S. PATENT DOCUMENTS

| | | | | |
|---|---|---|---|---|
| 4,579,837 | A | 4/1986 | Busch et al. | 502/167 |
| 4,849,076 | A | 7/1989 | Neckers | 204/157.15 |
| 5,835,840 | A | 11/1998 | Goswami | 422/186.3 |
| 6,036,738 | A | 3/2000 | Shanbrom | 55/524 |
| 6,190,437 | B1 | 2/2001 | Forsyth | 92/90 |
| 6,239,048 | B1 | 5/2001 | Wilson et al. | 442/123 |
| 6,322,614 | B1 | 11/2001 | Tillmans | 96/16 |
| 6,630,105 | B1 * | 10/2003 | O'Neill et al. | 422/24 |
| 6,692,694 | B1 * | 2/2004 | Curry et al. | 422/28 |

* cited by examiner

*Primary Examiner*—Steven VerSteeg
(74) *Attorney, Agent, or Firm*—Law Office of Dale B. Halling, LLC

(57) ABSTRACT

A system for chemical and biological decontamination has a source of oxygen. A reactor is coupled to the source oxygen. An optical source is coupled to the reactor. The system produces singlet delta oxygen that neutralizes chemical and biological contaminants.

17 Claims, 4 Drawing Sheets

10

SYSTEM FOR CHEMICAL AND BIOLOGICAL DECONTAMINATION

FIELD OF THE INVENTION

The present invention relates generally to the field of pathogen decontamination systems and more particularly to a system for chemical and biological decontamination.

BACKGROUND OF THE INVENTION

The need for effective chemical and biological decontamination systems was recognized by the military for many years before the anthrax attacks on the US congress. This need was based on knowledge of the capabilities of former cold war adversaries, third world antagonists and terrorist groups. One solution has been to use physical filters. These may work for individual units but cannot clean large volumes of air quickly and efficiently. Another solution has been to use catalysts such as $TiO_2$ and activate the catalyst with ultraviolet lamps. As the contaminated air passes over near the catalyst, hydroxyl radicals are created. The hydroxyl radicals cause the destruction of chemical and microbiological contaminants in the air. Unfortunately these systems require a certain level of humidity and therefor are not effective in dry environments such as airplanes.

Thus there exists a need for a chemical and biological decontamination system that can purify large quantities of air and does not require a certain level of humidity in the air.

DETAILED DESCRIPTION OF THE DRAWINGS

A system for chemical and biological decontamination has a source of oxygen. A reactor is coupled to the source oxygen. An optical source is coupled to the reactor. A wand is coupled to an output of the reactor in one embodiment. The system produces singlet delta oxygen that neutralizes chemical and biological contaminants. It is well known that single delta oxygen inactivates biogens and neutralizes chemical species. This body of research has not been reproduced herein.

Figure 1:
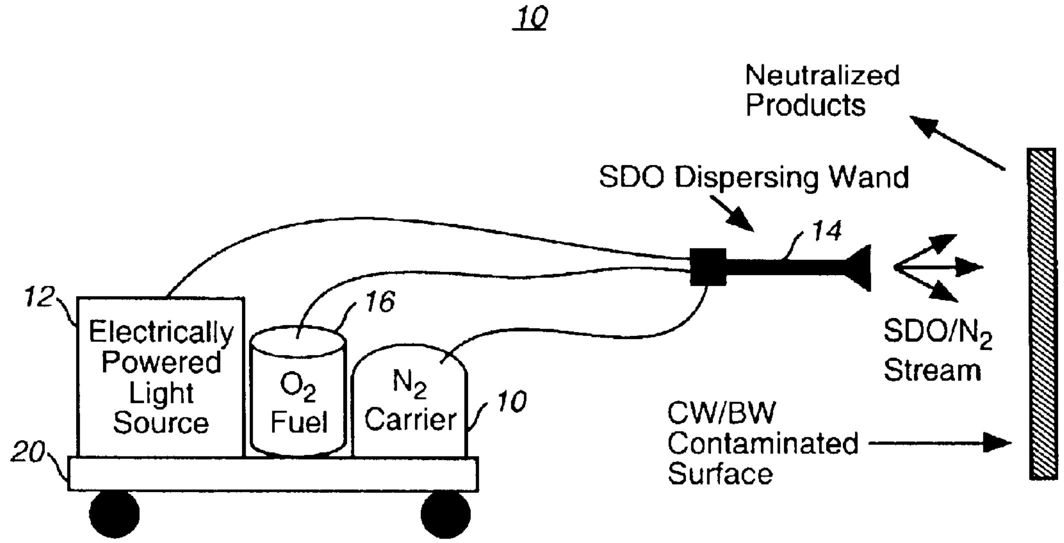
FIG. 1 is a block diagram of a system for chemical and biological decontamination in accordance with one embodiment of the invention.

FIG. 1 is a block diagram of a system 10 for chemical and biological decontamination in accordance with one embodiment of the invention. The system 10 has an electrically powered light source 12 that is coupled to a wand 14. A source of oxygen 16 and a source of nitrogen 18 are also coupled to the wand 14. The optical source 12 excites the oxygen 16 in the wand to form singlet delta oxygen (SDO) in a gaseous state. The SDO is then entrained in a flow of dry nitrogen to extend its lifetime and project it through the wand 14 toward a target surface for decontamination. In one embodiment, the system is transportable by placing the system on a cart 20. The nitrogen increases the lifetime of the SDO in air and therefor its effectiveness in decontaminating chemical and biological agents.

Figure 2:
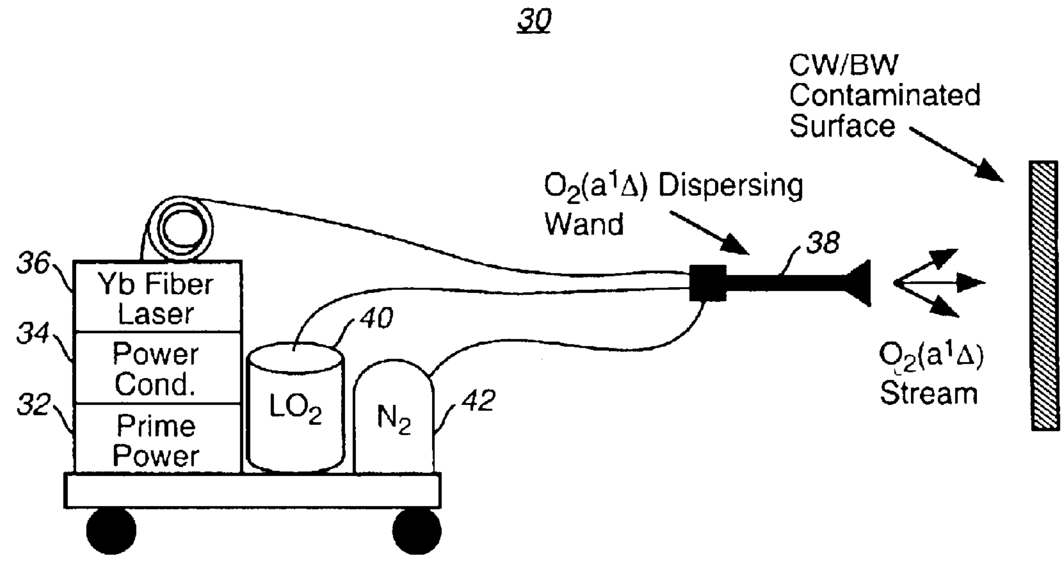
FIG. 2 is a block diagram of a system for producing singlet delta oxygen that may be used for chemical and biological decontamination in accordance with one embodiment of the invention.

FIG. 2 is a block diagram of a system 30 for producing singlet delta oxygen that may be used for chemical and biological decontamination in accordance with one embodiment of the invention. The system 30 has a prime power system 32 which may be a bank of batteries. A power conditioning system 34 is attached to the prime power system 32. A ytterbium (Yb) fiber laser(s) 36 is coupled to the power conditioning system 34. The Yb fiber laser 36 is coupled to the wand 38. A source of oxygen 40 and a source of nitrogen 42 are also connected to the wand 38. The optical source 36 excites the oxygen 40 in the wand to form singlet delta oxygen (SDO) in a gaseous state. The SDO is then entrained in a flow of dry nitrogen to extend its lifetime and project it through the wand 38 toward a target surface for decontamination. The system 30 may be used to produce singlet delta oxygen for other uses also, such as for the production of superconductors. The source of oxygen in one embodiment is liquid oxygen.

Figure 3:
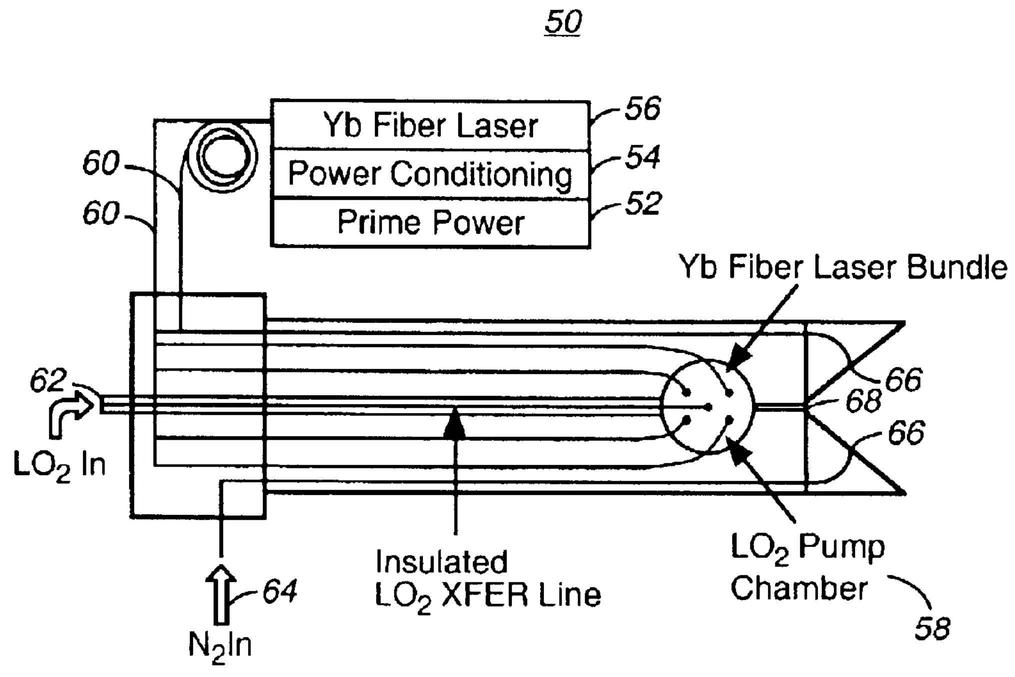
FIG. 3 is block diagram of a portion of a system for chemical and biological decontamination in accordance with one embodiment of the invention.

FIG. 3 is block diagram of a portion of a system 50 for chemical and biological decontamination in accordance with one embodiment of the invention. The system 50 has a prime power system 52, which may be a bank of batteries. A power conditioning system 54 is coupled to the prime power system 52. A ytterbium (Yb) fiber laser(s) 56 is coupled to the power conditioning system 54. The Yb fiber laser(s) 56 are coupled to a liquid oxygen pump chamber 58 by a plurality of optical fibers 60. A source of liquid oxygen 62 is also coupled to the liquid oxygen pump chamber 58 where the liquid oxygen is excited and vaporizes. Nitrogen 64 is pumped to the edge 66 of the output 68 of the liquid oxygen pump chamber 58.

Figure 4:
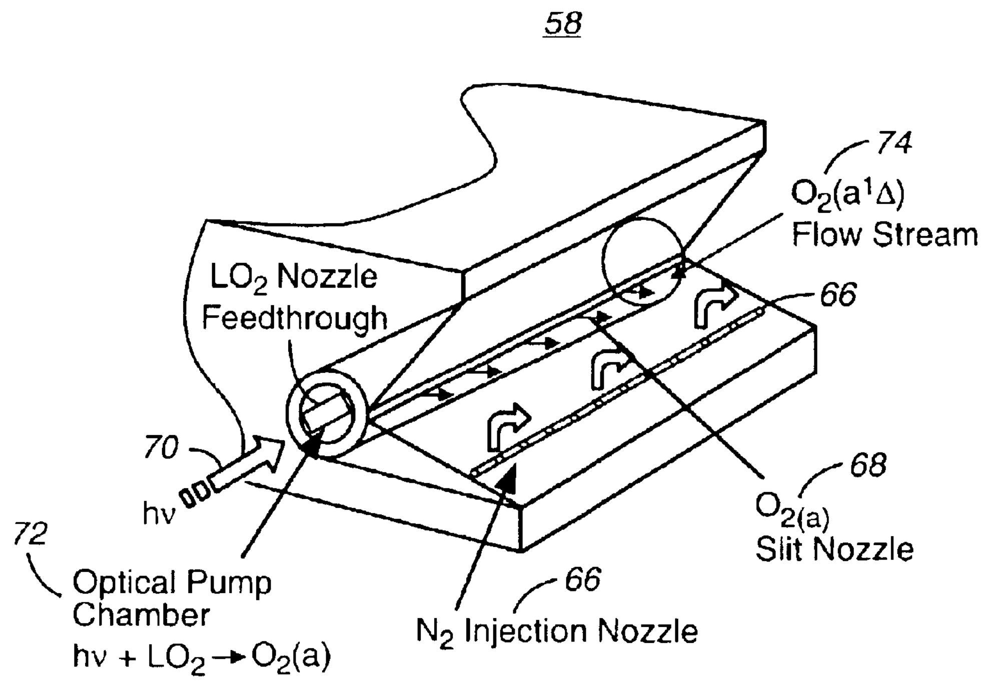
FIG. 4 is a perspective view of a optical pump chamber used in for a system for chemical and biological decontamination in accordance with one embodiment of the invention.

FIG. 4 is a perspective view of a optical pump chamber 58 used in for a system for chemical and biological decontamination in accordance with one embodiment of the invention. The optical pump chamber 58 shows the pump photons 70 entering a longitudinal end of the waveguide (reactor) 72. The gaseous singlet delta oxygen 74 exits the nozzle 68. The outlet 66 for the nitrogen is also shown.

Figure 5:
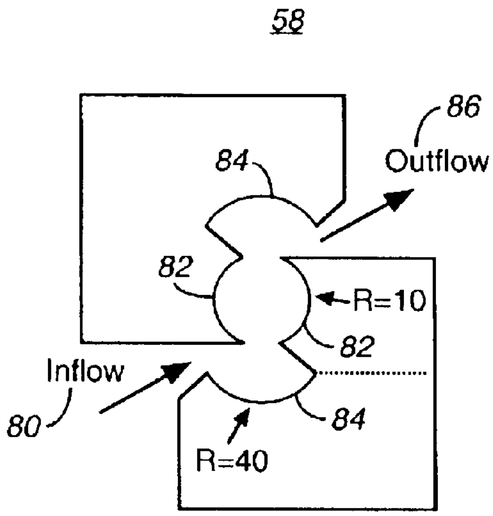
FIG. 5 is a cross sectional view of the optical pump chamber in accordance with one embodiment of the invention.

FIG. 5 is a cross sectional view of the optical pump chamber 58 in accordance with one embodiment of the invention. The liquid oxygen (high pressure oxygen) enters the reactor (optical pump chamber) 58 at an input 80. The structure of the reactor 58 has essentially two reflective cavities (pair of concentric mirrors and second pair of concentric mirrors) to confine the pump light in a horizontal and vertical direction. The interior structure of the reactor 58 is coated with a dielectric material to reflect the pump light. The pair of concentric mirrors 82 is concentric and confocal with the second pair of concentric mirrors 84. The reactor 58 has an output 86 in which the excited high pressure oxygen excites the reactor 58.

Figure 6:
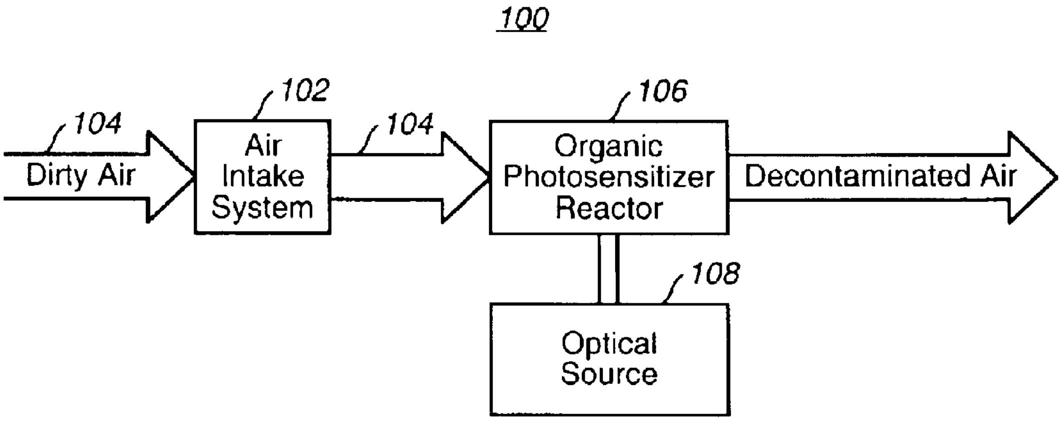
FIG. 6 is a block diagram of a system for chemical and biological decontamination in accordance with one embodiment of the invention.

FIG. 6 is a block diagram of a system 100 for chemical and biological decontamination in accordance with one embodiment of the invention. The system 100 has an air intake system 102 that pumps the contaminated air (compressed air) 104 into an organic photosensitizer reactor 106. An optical source 108 is connected to the organic photosensitizer reactor 106. The organic photosensitizer reactor 106 produces excited oxygen (e.g., singlet delta oxygen) that reacts with the contaminates and neutralizes them. The decontaminated air 110 is exhausted out of the organic photosensitizer reactor 106. In one embodiment the optical source 108 is a plurality of diodes or a ytterbium doped fiber laser or flash lamp. In one embodiment, the optical source 108 has an output in the red region of the optical spectrum. In one embodiment, the air intake system is a fan. A physical filter such as activated carbon may be used in combination with the system 100. The organic photosensitizer is a red photon absorbing material and may be a modified porphyrin (such as 5, 10, 15, 20 Tetrakis (2,6-dichlorophenyl) porphyrin); chlorin (such as 5, 10, 15, 20 Tetrakis (2,6-dichlorophenyl) chlorin); bacteriochlorin (such as 5, 10, 15, 20 Tetrakis (2,6-M-hydroxphenyl) bacteriochlorin); phthalocyanine (such as Ga(III)chloro sulfo-phthalocyanine); napthalocyanine (such as 2,11,20,29-tetrakis(1,1-dimethylethyl) chloroaluminum(III) napthalocycnine); porphine (such as 5,10,15,20-tetraphenyl chloroaluminum(III) Porphine); phorbide (such as Pheophorbide a); purpurin (such as tin etiopurpurin).

Figures 7, 8:
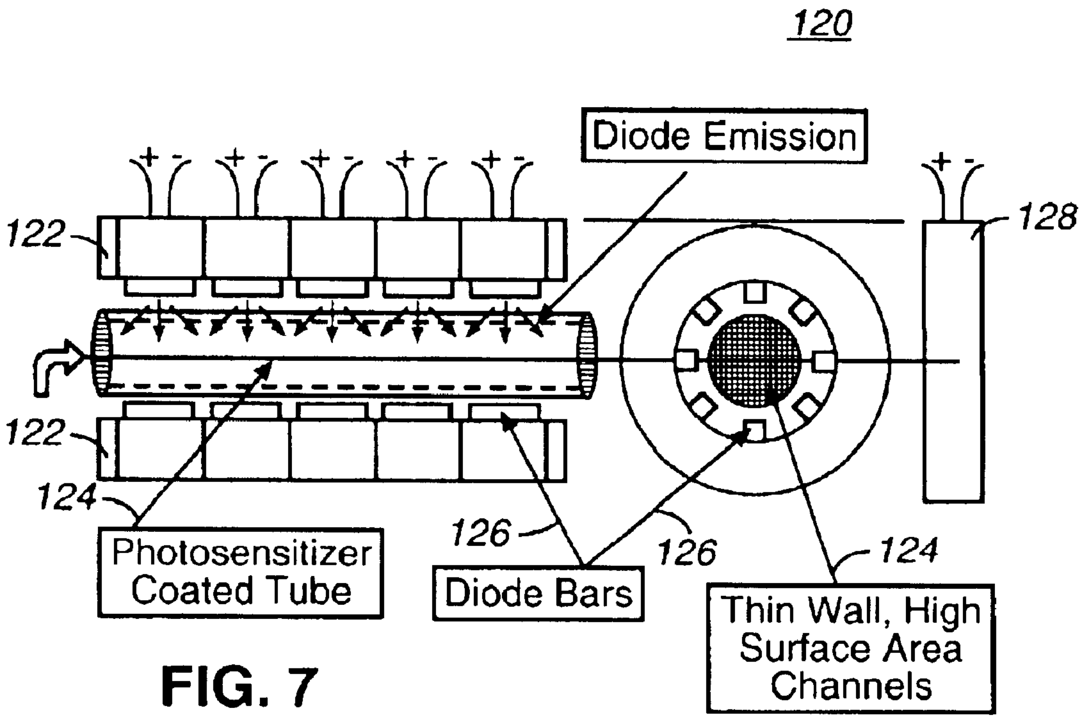
FIG. 7 is a side diagram of a photosensitizer reactor in accordance with one embodiment of the invention.
FIG. 8 is a partial end diagram of the photosensitizer reactor of FIG. 7 in accordance with one embodiment of the invention.

FIG. 7 is a side diagram of a photosensitizer reactor 120 in accordance with one embodiment of the invention. The reactor 120 has a diode array 122 surrounding a photosensitizer coated tube 124. In one embodiment, the reactor is a photosensitizer coated tube consisting of a thin-walled substrate with a network of high-surface area channels (plurality of micro flow channels). The combination of thin-walled, high surface area channels increases the production of singlet delta oxygen and the mass throughput of the system. In one embodiment, the tube and substrate are made of optical quality glass such as borosilicate, quartz or fused silica. In one embodiment, the tube is transmissive at the wavelength of the optical source. This allows the interior channels to become activated by the light. FIG. 8 is a partial end diagram of the photosensitizer reactor 120 of FIG. 7 in accordance with one embodiment of the invention. This diagram shows the diode bars 126 separate from the power conditioners 128 of the diode arrays 122. The end view shows the plurality of micro-channels in the ceramic photosensitizer reactor tube 124.

Thus there has been described a system for biological and chemical decontamination that uses the highly effective and short lived species of oxygen singlet delta oxygen. The system can decontaminate large quantities of contaminated air and is not limited by the humidity of the air.

It is well known that singlet delta oxygen inactivates biogens and neutralizes chemical species. This body of research has not been reproduced herein.

While the invention has been described in conjunction with specific embodiments thereof, it is evident that many alterations, modifications, and variations will be apparent to those skilled in the art in light of the foregoing description. Accordingly, it is intended to embrace all such alterations, modifications, and variations in the appended claims.

What is claimed is:

1. A system for chemical and biological decontamination or generating singlet delta oxygen comprising:

a source of oxygen;

a reactor coupled to the source oxygen; and an optical source coupled to the reactor.

2. The system of claim 1, wherein the reactor is an organic photosensitizer.

3. The system of claim 2, wherein the source of oxygen is a compressed air.

4. The system of claim 2, wherein the optical source is a diode array that shines light on the organic photosensitizer.

5. The system of claim 4, wherein the diode array has an output light in a 600–800 nanometer wavelength range.

6. The system of claim 2, wherein the organic photosensitizer is placed on a substrate having a plurality of micro flow channels.

7. The system of claim 1, further including a source of nitrogen coupled near an output of the reactor.

8. The system of claim 1, wherein the reactor is an optical waveguide.

9. The system of claim 1, wherein the reactor has a cross section that forms a pair of concentric mirrors.

10. The system of claim 9, wherein the cross section of the reactor forms a second pair of concentric mirrors that are concentric with the first pair of concentric mirrors.

11. The system of claim 10, wherein the optical source is a fiber laser.

12. The system of claim 1, wherein the optical source is a plurality of diodes.

13. The system of claim 1, wherein the optical source is coupled to a longitudinal end of the reactor.

14. The system of claim 13, wherein the reactor is an optical waveguide.

15. A system for chemical and biological decontamination, comprising:

an air intake system;

an organic photosensitizer reactor coupled to the air intake system; and an optical source coupled to the organic photosensitizer reactor.

16. The system of claim 15, further including a substrate on which an organic photosensitizer is deposited to from the photosensitizer reactor.

17. The system of claim 15, wherein the optical source has an output in a red region of the optical spectrum.

* * * * *